United States Patent
Schwartz et al.

(10) Patent No.: US 10,636,518 B2
(45) Date of Patent: Apr. 28, 2020

(54) AUTOMATED MEDICAL NOTE GENERATION SYSTEM UTILIZING TEXT, AUDIO AND VIDEO DATA

(71) Applicant: Virgo Surgical Video Solutions, Inc., San Francisco, CA (US)

(72) Inventors: Matthew Zane Schwartz, San Francisco, CA (US); David Oscar Guaraglia, San Francisco, CA (US); Ian Christopher Strug, Chicago, IL (US)

(73) Assignee: Virgo Surgical Video Solutions, Inc., San Francisco, CA (US)

( * ) Notice: Subject to any disclaimer, the term of this patent is extended or adjusted under 35 U.S.C. 154(b) by 0 days.

(21) Appl. No.: 15/929,037

(22) Filed: Aug. 8, 2018

(65) Prior Publication Data

US 2019/0057760 A1    Feb. 21, 2019

Related U.S. Application Data

(63) Continuation-in-part of application No. 15/793,502, filed on Oct. 25, 2017, now Pat. No. 10,342,410, and a continuation-in-part of application No. 15/929,035, filed on Aug. 2, 2018, now abandoned.

(60) Provisional application No. 62/542,555, filed on Aug. 8, 2017.

(51) Int. Cl.
*G16H 10/60* (2018.01)
*G06N 3/04* (2006.01)
*G16H 15/00* (2018.01)
*G06N 3/08* (2006.01)

(52) U.S. Cl.
CPC ............... *G16H 10/60* (2018.01); *G06N 3/04* (2013.01); *G06N 3/0445* (2013.01); *G06N 3/0454* (2013.01); *G06N 3/08* (2013.01); *G16H 15/00* (2018.01)

(58) Field of Classification Search
CPC ........ G16H 10/60; G06N 3/04; G06N 3/0445; G06N 3/0454
See application file for complete search history.

(56) References Cited

U.S. PATENT DOCUMENTS

| | | | | |
|---|---|---|---|---|
| 2011/0022412 | A1* | 1/2011 | Jackson | G06Q 50/22 705/3 |
| 2014/0019128 | A1* | 1/2014 | Riskin | G06Q 10/06 704/235 |
| 2014/0200931 | A1* | 7/2014 | Kulla | G06Q 30/012 705/4 |
| 2015/0347686 | A1* | 12/2015 | Ortiz | G06Q 50/22 705/3 |
| 2016/0287207 | A1* | 10/2016 | Xue | A61B 7/04 |
| 2017/0032221 | A1* | 2/2017 | Wu | G06K 9/6263 |
| 2017/0193361 | A1* | 7/2017 | Chilimbi | G06N 3/08 |
| 2017/0235888 | A1* | 8/2017 | Rahman | G06F 17/2785 705/3 |
| 2018/0150605 | A1* | 5/2018 | Co | G06F 17/2836 |

* cited by examiner

Primary Examiner — Eileen M Adams

(57) ABSTRACT

An automated medical note generation system utilizes text, audio and video data to automatically create medical notes in real-time from data sources that are generated actively during clinical events.

7 Claims, 2 Drawing Sheets

AUTOMATED MEDICAL NOTE GENERATION SYSTEM UTILIZING TEXT, AUDIO AND VIDEO DATA

CROSS-REFERENCE TO RELATED APPLICATIONS

This application is a continuation-in-part of application Ser. No. 15/793,502, filed on Oct. 25, 2017 and entitled "Automated System for Medical Video Recording and Storage," and application Ser. No. 15/929,035, filed on Aug. 2, 2018 and entitled "Endoscopic Video Recording System with Voice Control and Voice Annotation," and claims the benefit of priority under 35 § 119(e) to U.S. Provisional Patent Application No. 62/542,555, entitled "An Automated Medical Note Generation System Utilizing Text, Audio, and Video Data," filed on Aug. 8, 2017. Each of these applications is hereby incorporated by reference herein in its entirety

FIELD OF THE INVENTION

This disclosure pertains to systems and methods for automatically preparing medical notes during clinical events, and more particularly, to systems and methods for automatically preparing medical notes in real-time from text, audio and video data generated actively during clinical events.

BACKGROUND

In clinical medicine, physicians are faced with the challenging joint tasks of engaging with patients during exams, procedures, and diagnoses and taking detailed notes for medical records. It is well known that the performance of even well-trained professionals diminishes rapidly when multitasking. Thus, physicians typically employ a less than ideal workflow whereby they perform an exam, procedure, or diagnosis, then attempt to generate medical notes at a later time or date from memory. Unfortunately, it is also well known that human memory is imperfect, particularly in stressful and overworked environments. As such, when physicians are creating medical notes from recall, they are likely of lower quality than notes that could be created during the actual clinical event. The diminished quality of medical notes may likely lead to diminished quality of medical care.

Existing medical note systems require significant time and input from clinicians, yet they still result in suboptimal medical notes. In the most efficient existing systems, clinicians use template forms, which result in very similar notes across patients but provide little useful clinical information.

It would be advantageous to develop a medical note system that was able to automatically prepare high-quality medical notes information available in real-time during a clinical procedure, without the significant involvement of clinicians. U.S. Parent application Ser. No. 15/793,502, entitled "Automated System for Medical Video Recording and Storage" and incorporated by reference herein, discloses a system and method for automatically recording video images from a clinical procedure. U.S. application Ser. No. 15/929,035, filed on entitled "Endoscopic Video Recording System with Voice Control and Voice Annotation" and incorporated by reference herein, discloses a system and method for providing a clinician's audio annotations with video data during a clinical procedure.

In order to produce useful medical notes, it would be advantageous to employ an automated means for synthesizing data produced and recorded during a clinical procedure in accordance with. Neural networks and other related artificial intelligence systems are presently being employed for sophisticated data synthesis tasks. U.S. Pat. No. 8,428,935 to Waelti et al., which issued on Apr. 23, 2013 and is hereby incorporated by reference in its entirety herein, discloses a speech and textual analysis device incorporating a neural network for classifying and sorting speech and text data for the purpose of constructing a search and/or classification catalog.

U.S. Pat. No. 9,754,584 to Parada San Martin et al., which issued on Sep. 5, 2017 and is hereby incorporated by reference in its entirety herein, discloses a neural network feature extractor for keyword or key phrase spotting.

U.S. Pat. No. 9,456,174 to Boyle et al., which issued on Sep. 27, 2016 and is hereby incorporated by reference in its entirety herein, discloses a neural network-based video editing system for automatically editing video recorded by a plurality of video recording systems in accordance with user pre-determined, pre-recorded video editing decisions and rules.

SUMMARY

By way of example, aspects of the present disclosure are directed to a system that creates notes in real-time from data sources that are generated actively during clinical events such as text, clinician audio and clinical video. This both expedites the workflow and creates higher quality notes).
1. In particular, a computer-implemented for preparing medical notes for a clinical event, the system comprising:
   a. a first neural network for processing textual data associated with medical records for a clinical patient;
   b. a second neural network for processing video data recorded for the clinical event;
   c. a third neural network for processing audio data including voice data for a clinician participating in the clinical event; and
   d. a fourth neural network for processing the processed textual data, processed video data and processed audio data to prepare the medical notes.

In accordance with another aspect of the disclosure, the first neural network, second neural network and third neural network of the computer-implemented system each comprise a long term short memory (LSTM).

In accordance with another aspect of the disclosure, each of the second neural network and third neural network further comprise a convolutional neural network (CNN) coupled to a respective LSTM.

In accordance with yet another aspect of the present disclosure, the fourth neural network is capable to prepare the medical notes as one of textual data, video data or audio data, or as a combination of two or more of the textual data, video data or audio data.

In accordance with a further aspect of the present disclosure, the computer-implemented system is operative to prepare the medical notes substantially in real-time at the conclusion of the clinical event.

This SUMMARY is provided to briefly identify some aspects of the present disclosure that are further described below in the DESCRIPTION. This SUMMARY is not intended to identify key or essential features of the present disclosure nor is it intended to limit the scope of any claims.

BRIEF DESCRIPTION OF THE DRAWINGS

A more complete understanding of the present disclosure may be realized by reference to the accompanying drawing in which.

DETAILED DESCRIPTION

Figure 1:
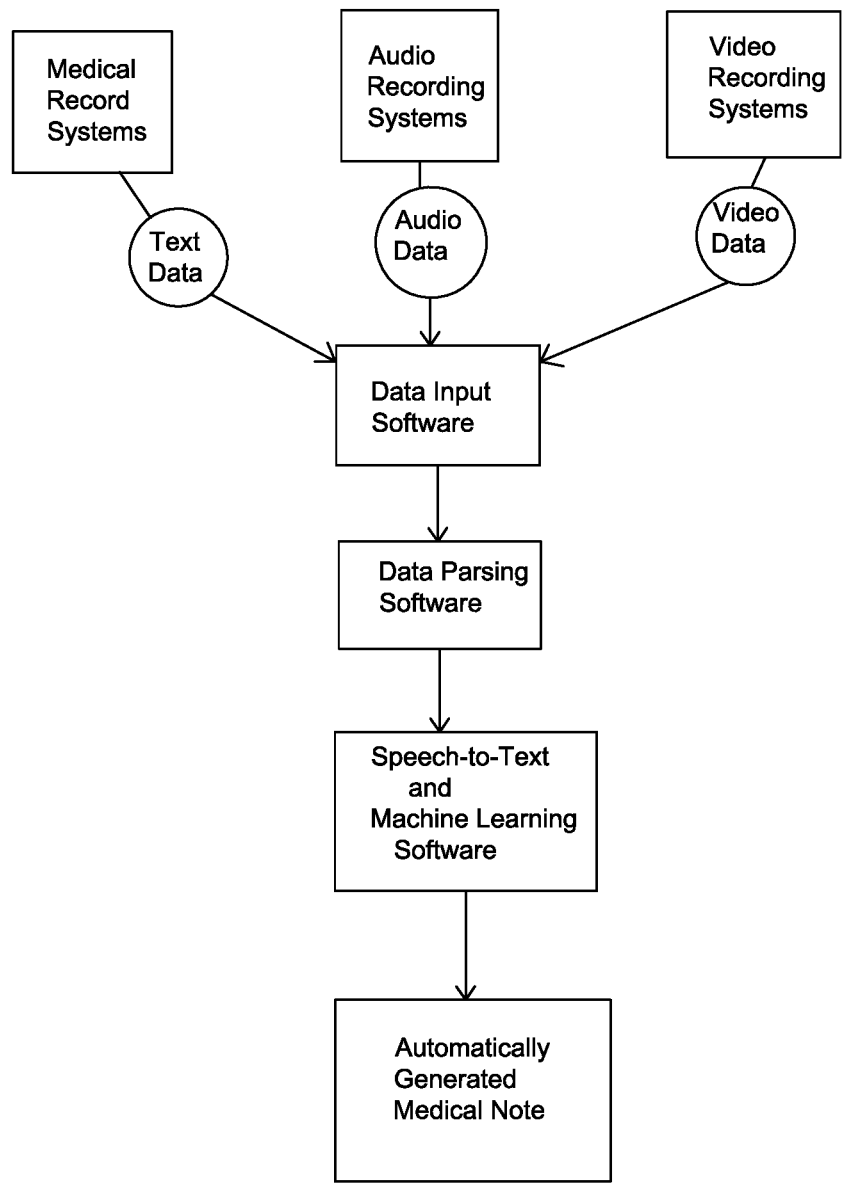
FIG. 1 provides a schematic drawing that illustrates a system for automated medical note generation according to aspects of the present disclosure.

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements later developed that perform the same function, regardless of structure.

Unless otherwise explicitly specified herein, the drawings are not drawn to scale.

In the following description, the same reference signs are used for the same and similarly acting parts.

As described above, in clinical medicine, physicians are faced with the challenging joint tasks of engaging with patients during exams, procedures, and diagnoses and taking detailed notes for medical records. It is well known that the performance of even well-trained professionals diminishes rapidly when multitasking. Thus, physicians typically employ a less than ideal workflow whereby they perform an exam, procedure, or diagnosis, then attempt to generate associated medical notes at a later time or date from memory. Unfortunately, it is also well known that human memory is imperfect, particularly in stressful and overworked environments. As such, when physicians are creating medical notes from recall, they are likely to be of lower quality than notes that could be created during the actual clinical event. The diminished quality of medical notes likely leads to diminished quality of medical care.

Aspects of the present disclosure are directed to a system and method that use data preferably including medical record text, audio, and video, to automatically generate high quality medical notes during or immediately after clinical events. The system employs a variety of component elements using computer vision, machine learning, and natural language processing to transform information from these disparate data sources into high quality medical notes. By automatically creating the medical notes during the clinical event, high-quality medical notes are produced while at the same time achieving an improved clinical workflow.

Existing technology enables clinicians to take medical notes by writing, direct computer entry, using computer template forms, or with dictation software. However, each of these conventional methods disrupt the clinical workflow. The system disclosed herein improves over these conventional methods by realizing a truly automated, real-time note generation by utilizing various data sources with speech-to-text, natural language processing, computer vision, and machine learning software, without disrupting the clinical workflow.

Existing systems do not work well in part because they most often rely on clinicians to recall experiences from memory well after the time at which clinical events are carried out. This often happens during times when clinicians are very busy, or hours or even days after the clinical event took place. This is unlikely to result in quality medical notes.

This system and methods disclosed herein create notes in real-time from a variety of data sources that are generated actively during clinical events, such as associated text, and clinician audio and clinical video recordings. Automatically generating notes in real time based on these multiple data sources both expedites the workflow and creates higher quality notes.

A system in accordance with aspects of the present disclosure may preferably include: 1) medical notes, 2) a medical record system. 3) clinician audio, 4) an audio recording system, 5) medical video, 6) a medical video recording system, 7) a computer system, 8) software for integrating data sources, 9) software for generating medical notes from data sources, 10) machine learning software for contextualizing notes from the data sources, and 11) training data.

The disclosed system may for example be operated as follows. Medical notes (1) from the medical record system (2), clinician audio (3) from the audio recording system (4), and medical video (5) from the medical video recording system (6) are collected and/or transmitted to the computer system (7). The computer system (7), which may for example be either a local system or a cloud based system, contains software for integrating data sources (8) and software for generating medical notes from data sources (9). Additionally, the computer system (7) contains machine learning software for contextualizing notes from data sources (10). In order to perform this function, the machine learning software is preferably trained algorithmically using training data (11), which is comprised of appropriate medical notes (1), clinician audio data (3), and medical video data (5). An exemplary system for automatically generating medical notes is illustrated in FIG. 1

The computer system (7) used for generating the medical notes is operable for aggregating relevant data streams, including but not limited to audio, video, and text. Specifically, and as illustrated in FIG. 1, a combination of audio information recorded by the clinician, video recorded from the clinical event, and text from an associated medical record are ingested and parsed by the computer system. These data streams are then preferably pushed to a pre-trained machine learning software system that is able to make inferences from data. In this case, the machine learning software system will be operable to infer an appropriate, high-quality, medical note from the audio, video, and/or text data that has been input. This medical note may then optionally be reviewed and/or edited by the clinician prior to entering it into an official medical record system.

Figure 2:
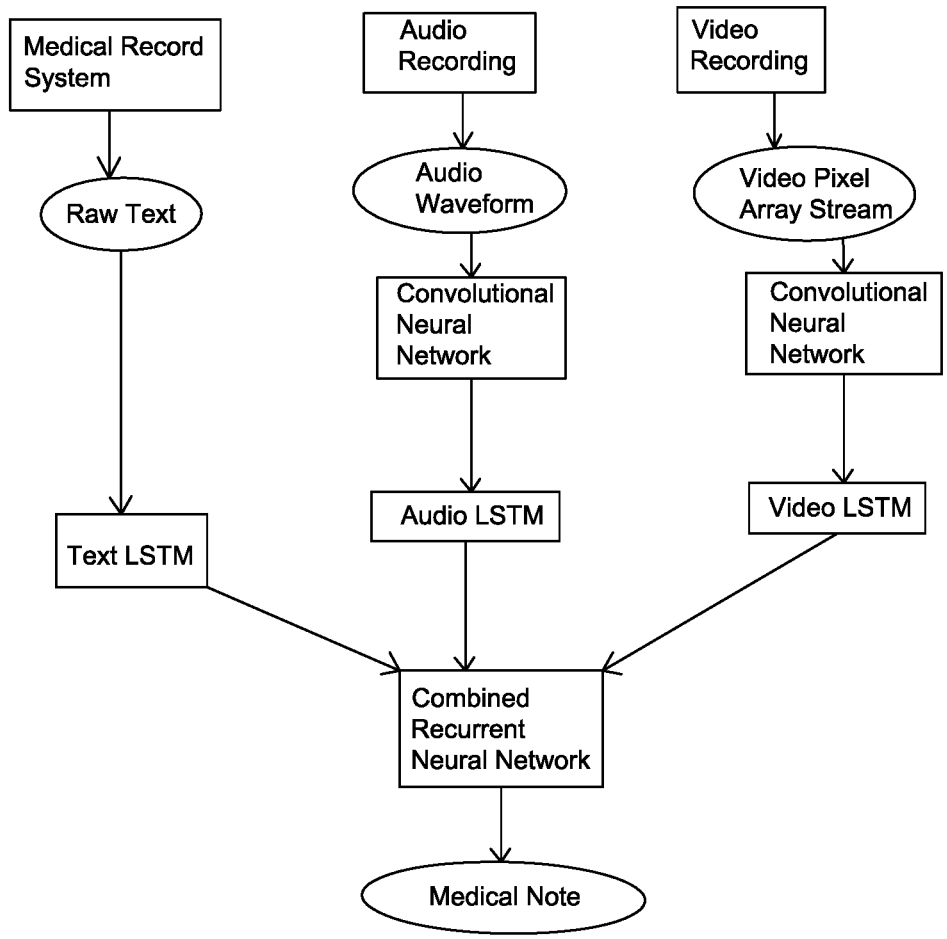
FIG. 2 provides a schematic drawing that illustrates an exemplary embodiment of the system depicted in FIG. 1.

Once sufficient audio, video, and text data has been aggregated, this data can be used as training data for a machine learning software system that takes the audio, video, and text data as potential input and outputs a medical note. This machine learning system may for example be comprised of neural networks including, but not limited to, deep neural networks, convolutional neural networks, recurrent neural networks, and long short-term memory networks ("LSTMs"). FIG. 2 illustrates an exemplary machine learning system according to aspects of the present disclosure, which includes convolutional neural networks ("CNNs") for processing the audio and video recording data, LSTMs for processing text, audio and video data, and a combined recurrent neural network ("RNN") for integrating the audio, video, and text data to produce the medical notes. In practice, the data used to generate medical notes may be limited to any of audio, video, or text data, or any combination thereof.

To make this invention, one must first aggregate the requisite training data sets. A critical mass of data is required to train the machine learning software to a suitable accuracy level. Once the machine learning software system has been trained, it can be deployed in the computer system for inference. The inference process works algorithmically, whereby relevant data streams are input and a medical note is output. Machine learning system may for example be simply driven by speech-to-text conversion, or extended to include further processing performed by a combination of convolutional and recurrent neural networks.

The various data sources can be input to the system in any number of configurations. In addition to the exemplary system illustrated in FIG. 2, there are many other possible configurations for the machine learning software system (including neural network and other software configurations).

It will be understood that, while various aspects of the present disclosure have been illustrated and described by way of example, the invention claimed herein is not limited thereto, but may be otherwise variously embodied within the scope of the following claims. For example, while this examples have been described for the medical note taking field, principles of the present disclosure may be easily applied to other fields where high quality note-taking is needed to assist or record the result of complex human-interactive procedures (for example, dentistry, cooking, machine assembly and repair, and the like).

We claim:

1. A computer-implemented machine learning system for preparing medical notes for a clinical event, the system comprising:
   a. a first processing element for processing textual data associated with medical records for a clinical patient;
   b. a second processing element for processing video data recorded for the clinical event;
   c. a third processing element for processing audio data including voice data for a clinician participating in the clinical event; and
   d. a combined recurrent neural network (RNN) for integrating the processed textual data, processed video data and processed audio data to contextualize and prepare the medical notes, wherein the combined RNN has been trained by a plurality of training data sets aggregating completed medical notes with associated audio data and video data.

2. The computer-implemented system of claim 1, wherein the combined RNN is capable to prepare the medical notes as at least one of textual data, video data or audio data.

3. The computer-implemented system of claim 2, wherein the combined RNN is capable to prepare the medical notes as a combination of two or more of textual data, video data or audio data.

4. The computer-implemented system of claim 1, wherein the computer-implemented system is operative to prepare the medical notes substantially in real-time at the conclusion of the clinical event.

5. The computer-implemented system of claim 1, wherein:
   the first processing element comprises a first neural network;
   the second processing element comprises a second neural network; and
   the third processing element comprises a third neural network.

6. The computer-implemented system of claim 5, wherein the first neural network, second neural network and third neural network each comprise a long term short memory (LSTM).

7. The computer-implemented system of claim 6, wherein each of the second neural network and third. neural network further comprise a convolutional neural network (CNN) coupled to a respective LSTM.

* * * * *